US009119806B2

(12) United States Patent
Nauwynck et al.

(10) Patent No.: US 9,119,806 B2
(45) Date of Patent: Sep. 1, 2015

(54) CULTURING CIRCULAR SSDNA VIRUSES FOR THE PRODUCTION OF VACCINES

(76) Inventors: Hans Nauwynck, Zomergem (BE); Gerald Misinzo, Sengerema (TZ); Sven Arnouts, Bertem (BE)

( * ) Notice: Subject to any disclaimer, the term of this patent is extended or adjusted under 35 U.S.C. 154(b) by 0 days.

(21) Appl. No.: 12/510,844

(22) Filed: Jul. 28, 2009

(65) Prior Publication Data

US 2010/0166705 A1 Jul. 1, 2010

Related U.S. Application Data

(62) Division of application No. 11/680,420, filed on Feb. 28, 2007, now Pat. No. 7,566,562.

(51) Int. Cl.

| | |
|---|---|
| ***C12N 7/00*** | (2006.01) |
| ***A61K 39/12*** | (2006.01) |
| ***A61K 39/39*** | (2006.01) |
| ***A61K 38/21*** | (2006.01) |
| *A61K 39/00* | (2006.01) |

(52) U.S. Cl.

CPC ................ *A61K 39/12* (2013.01); *A61K 38/21* (2013.01); *A61K 39/39* (2013.01); *C12N 7/00* (2013.01); *A61K 2039/5254* (2013.01); *A61K 2039/552* (2013.01); *A61K 2039/55522* (2013.01); *C12N 2750/10034* (2013.01)

(58) Field of Classification Search

None

See application file for complete search history.

(56) References Cited

U.S. PATENT DOCUMENTS

| | | | |
|---|---|---|---|
| 7,300,785 | B2 | 11/2007 | Meerts et al. |
| 2007/0184544 | A1 | 8/2007 | Nauwynck et al. |
| 2008/0226594 | A1 | 9/2008 | Nauwynck et al. |

FOREIGN PATENT DOCUMENTS

| | | | |
|---|---|---|---|
| EP | 1 688 485 | A1 | 9/2006 |
| WO | WO 01/16330 | | 3/2001 |

OTHER PUBLICATIONS

Hino et al. "Torque teno virus (TTV): current status." Reviews in Medical Virology 17:45-57, 2007.*

Stewart et al ["Baculovirus expression of beak and feather disease virus (BFDV) capsid protein capable of self-assembly and haemagglutination," Journal of Virological Methods 141 (2007) 181-187].*

Scott et al ["Serological diagnosis of goose circovirus infections," Avian Pathology (Dec. 2006) 35(6), 495-499].*

Smyth ["Investigation of avian circovirus infection and attempted development of an infection study model of circovirus infection in ducks or geese," CRIS project report 2009, downloaded from the internet Jan. 5, 2011 << http://www.reeis.usda.gov/web/crisprojectpages/215225.html>>9 .*

Jurkovitz et al (Kidney International 42:595-601, 1992).*

Allan et al. "A sequential study of experimental infection of pigs with porcine circovirus and porcine parvovirus: immunostaining of cryostat sections and virus isolation," (2000) J Vet Med B. 47, 81-94.

Allan et al. "Experimental infection of colostrum deprived piglets with porcine circovirus 2 (PCV2) and porcine reproductive and respiratory syndrome virus (PRRSV) potentiates PCV2 replication," (2000) Arch Virol. 145, 2421-2429.

Allan et al. "Pathogenesis of porcine circovirus; experimental infections of colostrum deprived piglets and examination of pig foetal material," (1995) Vet. Microbiol. 44, 49-64.

Allan and Ellis, "Porcine circoviruses: a review," *J. Vet. Diagn. Invest.* 12:3-14, 2000.

Biagini "Human circoviruses," (2004) Vet. Microbiol. 98, 95-2004.

Blanchard et al. "Protection of swine against post-weaning multisystemic wasting syndrome (PMWS) by porcine circovirus type 2 (PCV2) proteins," (2003) Vaccine 21, 4565-4575.

Darwich et al., "Cytokine profiles of peripheral blood mononuclear cells from pigs with postweaning multisystemic wasting syndrome in response to mitogen, superantigen or recall viral antigens," Journal of General Virology, 88:3435-57 (2003).

Edwards and Sands, "Evidence of circovirus infection in British pigs," *Vet. Rec.* 134:680-681, Abstract only (1994).

Familletti et al. "A convenient and rapid cytopathic effect inhibition assay for interferon," (1981) Methods in Enzymology 78, 387-394.

Fenaux et al. "A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs." *J. Viral.* 78: 6297-6303 (2004).

Jung et al., "Optimization of reovirus production from mouse L-929 cells in suspension culture," *Biotechnol. Bioeng.* 85:750-760 (2004).

Krakowka et al. "Activation of the immune system is the pivotal event in the production of wasting disease in pigs infected with porcine circovirus-2 (PCV-2)," (2001) Vet Pathol. 38, 31-42.

Larghi et al. "Rabies virus inactivation by binary ethylenimine: new method for inactivated vaccine production," (1980) J. Clin Microbiol 11, 120-122.

Lefevre et al. "Production, purification and biological properties of an *Escherichia coli*-derived recombinant porcine alpha interferon," (1990) J Gen Virol. 71, 1057-1063.

Meehan et al. "Characterization of novel circovirus DNAs associated with wasting syndromes in pigs," (1998) J. Gen Virol. 79, 2171-2179.

Meerts et al. "Enhancement of porcine circovirus 2 replication in porcine cell lines by IFN-y before and after treatment and by IFN-a after treatment." *J. of Interferon and Cytokine Research* 25: 684-693 (2005).

Misinzo et al. "Binding and entry characteristics of porcine circovirus 2 in cells of the porcine monocytic line 3D4/31," (2005) J. Gen Virol 86, 2057-68.

(Continued)

*Primary Examiner* — Mary E Mosher

(74) *Attorney, Agent, or Firm* — Clark & Elbing LLP

(57) ABSTRACT

The present invention relates to the use of interferon in the in vitro cultivation of animal circular ssDNA virus such as Porcine Circovirus 2 or human TT virus in an animal cell line. Increased titres of animal circular ssDNA virus are obtained by addition of interferons or agents which ensure the production of endogenous interferons by said cell line and/or by the reduction of endosomal-lysosomal system acidification.

14 Claims, 5 Drawing Sheets

(56) References Cited

OTHER PUBLICATIONS

Misinzo et al., "Increased Yield of Porcine Circovirus-2 by a Combined Treatment of PK-15 Cells with Interferon-Gamma and Inhibitors of Endosomal-Lysosomal System Acidification," *Arch. Virol.* 153(2):337-342 (2008).

Misinzo et al., "Inhibition of Endosome-Lysosome System Acidification Enhances Porcine Circovirus 2 Infection of Porcine Epithelial Cells," J. Virol. 82:1128-1135, 2008.

Moreno et al. "Response of TT virus to IFN plus ribavirin treatment in patients with chronic hepatitis C," World J. Gastroenterol (2004) 1, 143-146.

Pestka. "Interferon standards and general abbreviations," (1986) Methods in Enzymology 119, 14-23.

Rubinstein et al. "Convenient assay for interferons," (1981) J. Virol. 37, 755-758.

Sanchez et al. "Change of porcine circovirus 2 target cells in pigs during development from fetal to early postnatal life," (2003) Vet Microbiol 95, 15-25.

Scodeller et al. "Inactivation of foot-and-mouth disease virus vaccine strains by activation of virus-associated endonuclease," (1984) J. Gen Virol., 65, 1567-1573.

Shibayama et al. "Inverse relationship between the titre of TT virus DNA and the CD4 cell count in patients infected with HIV," (2001) AIDS 15, 563-570.

Touinssi et al. "TT virus infection: prevalence of elevated viraemia and arguments for the immune control of viral load," J. Clin Virol. (2001) 21, 135-141.

Verfaillie et al. "Comparative analysis of porcine cytokine production by mRNA and protein detection," (2001) Vet Immunol Immunopathol, 38, 57-73.

Von Neiderhausern et al. "Cloning and expression in mammalian cells of porcine tumor necrosis factor alpha: examination of biological properties," (1993) Vet Immunol Immunopathol, 38, 57-73.

Weingartl et al. "Continuous porcine cell lines developed from alveolar macrophages: Partial characterization and virus susceptibility," (2002) J. Virol Methods. 10, 203-216.

Xia et al. "Cloning and expression of interferon-α/γfrom a domestic porcine breed and its effect on classical swine fever virus," (2005) Vet Immunol Immunopathol. 104, 81-89.

Office Action for U.S. Appl. No. 11/275,842, mailed Oct. 11, 2006.

Notice of Allowance for U.S. Appl. No. 11/275,842, mailed Apr. 6, 2007.

Extended European Search Report (EPO Form 1507N) for EP Application No. 06002030.2, May 30, 2006.

* cited by examiner

CULTURING CIRCULAR SSDNA VIRUSES FOR THE PRODUCTION OF VACCINES

CROSS REFERENCE TO RELATED APPLICATIONS

This application is a divisional of U.S. patent application Ser. No. 11/680,420, filed Feb. 28, 2007 now U.S. Pat. No. 7,566,562, which is a continuation-in-part of U.S. patent application Ser. No. 11/275,842, filed Jan. 31, 2006 now U.S. Pat. No. 7,300,785, which, in turn, claims benefit of U.S. Provisional Application Ser. No. 60/649,738, filed Feb. 3, 2005, the disclosures of which are incorporated by reference.

FIELD OF THE INVENTION

The present invention relates to cell culture methods for the in vitro cultivation of viruses (more in particular animal circular ssDNA viruses), which are of use in the production of vaccines, as well as the vaccines produced. The invention further relates to in vitro methods for the diagnosis of animal circular ssDNA viral infection.

BACKGROUND

Animal circular ssDNA viruses are a group of viruses of pathogenic importance. Human circular ssDNA viruses have been detected in patients with hepatitis of unknown aetiology. The titre of human TTV virus is also significantly higher in HIV-infected patients with AIDS, AIDS patients with a low CD4 T cell count, or patients with high HIV viral loads [Shibayama et al. (2001) *AIDS* 15, 563-570]. Touinssi et al. [*J. Clin Virol*. (2001) 21, 135-141] report a relationship between the prevalence of elevated viral loads of TTV virus and the level of immunocompetence of the populations studied and suggest that stimulation of the immune system by an interferon treatment was able to clear TTV viraemia. Moreno et al. (*World J Gastroenterol* (2004) 1, 143-146) however found that administration of PEG-IFN plus ribovarin could not induce a TTV sustained response in patients infected with hepatitis C.

Porcine circoviruses are associated with the occurrence of postweaning multisystemic wasting syndrome (PMWS) in pigs. Porcine circovirus 2 (PCV2) is a member of the family of Circoviridae. It is a very small virus with a relatively simple structure. The PCV2 viral genome does not code for a viral DNA-polymerase, making it dependent on cellular enzymes to complete its infectious cycle.

When PCV2 is inoculated in susceptible pigs, a high variation in virus replication is observed. It has been observed that PCV2 is able to replicate better in a host that is simultaneously inoculated with other viruses such as porcine reproductive and respiratory syndrome virus (PRRSV) [Allan et al. (2000) *Arch Virol*. 145, 2421-2429] or porcine parvovirus (PPV) [Allan et al. (2000) *J Vet Med B*. 47, 81-94]. A general stimulation of the immune system with keyhole limpet hemocyanin [Krakowka et al. (2001) *Vet Pathol*. 38, 31-42] has also been found to ameliorate the replication of PCV2 in the host.

It has been shown for PCV2 that inhibition of endosomal-lysosomal system acidification in a monocytic cell line reduced PCV2 infection (Misinzo et al., 2005. J Gen Virol. 86:2057-68). These data demonstrated that PCV2 requires an acidic environment for infection of a monocytic cell line.

Many cytokines are capable of modulating the susceptibility of the host to a viral infection. The most studied and best understood is the anti-viral effect of type I interferons (IFN-alpha and IFN-beta). But also other cytokines such as tumour necrosis factor alpha (TNF-alpha) and type II interferon (IFN-gamma) have been shown to influence infection. The antiviral effect of interferons has been demonstrated for many viruses and has been found to be so consistent and potent that humans and animals are routinely administered recombinant interferon (IFN-alpha) for the treatment of viral infections.

SUMMARY OF THE INVENTION

The present invention is based on the surprising observation, that type I and type II interferons have an enhancing effect on the viral titre obtained in cell cultures after infection in vitro with animal circular ssDNA virus, more particularly porcine circovirus 2. In addition it was observed that, when cultivating PCV2 in PK-15 epithelial cells in the presence of inhibitors of endosomal-lysosomal system acidification, the viral titre obtained in the cell cultures is further increased and this independently of the effect of interferons. The combination of interferons and endosomal-lysosomal system acidification inhibitors generates a synergistic effect.

A first aspect of the present invention relates to the use of an interferon-containing medium for the cultivation of animal circular ssDNA virus in an animal cell line.

According to a first embodiment of this aspect of the invention methods are provided for the in vitro cultivation of an animal circular ssDNA virus comprising the step of inoculating cells of a continuous animal cell line in a culture medium with the circular ssDNA virus, thereby ensuring that the culture medium contains interferon. Different methods for ensuring that the medium contains interferon are envisaged. According to a specific embodiment a method is provided for the in vitro cultivation of an animal circular ssDNA virus comprising the steps of a) inoculating cells of a cell line, more particularly a continuous animal cell line, in culture medium with a circular ssDNA virus and b) administering an exogenous interferon or an agent which induces the endogenous production of an interferon by said cells. In view of the fact that the object of the methods according to this aspect of the invention is the generation of PCV2 viral particles, the methods of the invention typically additionally comprise the step of isolating PCV2 particles from the medium and/or infected cells of the continuous animal cell line.

A second aspect of the present invention relates to the cultivation of animal circular ssDNA virus in an animal cell line, whereby it is ensured that endosomal-lysosomal system acidification in the animal cell line is reduced.

Accordingly, the present invention provides methods for the in vitro cultivation of an animal circular ssDNA virus comprising the step of (a) inoculating cells of a continuous animal cell line in a culture medium with the circular ssDNA virus, and (b) cultivating the continuous animal cell line thereby ensuring that endosomal-lysosomal system acidification is reduced in the continuous animal cell line. As the object of the methods of the invention is the generation of the animal circular ssDNA virus or parts thereof, the methods of the invention generally comprise a further step (c), wherein the animal circular ssDNA virus is isolated from the medium and/or infected cells of the continuous animal cell line.

Depending on the tools used to ensure the reduction of endosomal-lysosomal system acidification, this can be ensured before, during and/or after the inoculation with the circular ssDNA virus.

In one embodiment of the methods of the invention, the continuous animal cell line is cultivated in the presence of an inhibitor of endosomal-lysosomal system acidification, more particularly, a lysosomotropic agent capable of reducing endosomal-lysosomal system acidification. Most particularly, the use of ammonium chloride, chloroquine diphosphate and monensin as lysosomotropic agents are envisaged.

In further particular embodiments, the methods of the invention comprise the steps of: (a) inoculating cells of a continuous animal cell line in culture medium with a circular ssDNA virus and, (b) cultivating the inoculated continuous animal cell line in the presence of an agent capable of inhibiting endosomal-lysosomal system acidification.

Yet a further aspect of the present invention relates to the use of both the presence of interferon and the effect of endosomal-lysosomal system acidification for improving methods for the cultivation of animal circular ssDNA virus in an animal cell line.

Accordingly, methods are provided wherein a continuous animal cell line, prior to, during or after inoculation, is cultivated in the presence of Interferon and simultaneously or sequentially reduction of endosomal-lysosomal system acidification is ensured.

In one embodiment of this aspect of the invention, methods are provided comprising the steps of (a) inoculating cells of a continuous animal cell line in culture medium with a circular ssDNA virus, (a') administering an exogenous interferon or an agent which induces the endogenous production of an interferon by the cells of the cell line and, (b) cultivating the continuous animal cell line in the presence of an agent capable or inhibiting endosomal-lysosomal system acidification, whereby the steps are not necessarily in that order. Where the steps of the method are in that order, the methods of the invention may optionally comprise, between steps (a') and (b) a change of cultivation medium.

According to particular embodiments the methods according to the different aspects of the invention are used for cultivating viruses belonging to the group of Circoviruses, most particularly Porcine Circovirus 2 (PCV2).

According to further particular embodiments of the methods of the invention, the cell line use in the methods of the invention is an non-human animal cell line, more particularly a porcine cell line, such as, but not limited to PK-15, ST, SK or 3D4/31. In particular embodiments, the cell line is an epithelial cell line.

In particular embodiments, the methods of the invention encompasses ensuring the presence of interferon in the medium of the cell lines. This can be achieved either by contacting the cell line with interferons, e.g. by adding one or more exogenous interferons, such as interferon-alpha or interferon-gamma to the medium. According to particular embodiments, the one or more interferons are added to the culture medium at a concentration of at least 2 U/ml medium. Addition of interferons to the medium can be performed before, during or after inoculation of the cell line with the animal circular ssDNA virus.

According to further embodiments of the methods of the present invention which encompass ensuring the presence of interferon in the medium of the cell lines, this is achieved by the endogenous production of interferons by the continuous cell line. In these embodiments, a continuous cell line capable of producing interferons is used. The production of interferons can be inherent to the animal cell line used or can be the result of transfection with a polynucleotide which ensures interferon production, either constitutively or by way of an inducible promoter whereby after transfection, stimulation of the inducible promoter by an agent results in interferon production by the cell line. Thus, according to these embodiments a transgenic cell line, i.e. a cell line comprising a foreign DNA which ensures production of interferon, such as a foreign DNA encoding an interferon, is used in the methods of the invention.

According to another aspect of the invention cultivation media are provided which comprise both animal circular ssDNA virus and at least 2 U/ml interferon and/or an agent capable of inhibiting endosomal-lysosomal system acidification. According to the present invention such media can be used for the development of a vaccine.

Thus, according to yet another aspect of the invention methods are provided for producing a vaccine. The methods of the invention allow a more cost-efficient way of producing animal circular ssDNA virus which can further be processed into a vaccine. In one embodiment, the method for producing a vaccine will comprise the steps of inoculating a continuous cell line with a circular ssDNA virus and ensuring that the medium of the continuous cell line comprises interferon, more particularly at a concentration of at least 2 U/ml. In another embodiment, the methods for producing a vaccine will comprise the steps of inoculating cells of a continuous animal cell line in a culture medium with the circular ssDNA virus, thereby ensuring, prior to and/or inoculation, the reduction/inhibition of endosomal-lysosomal system acidification in the continuous animal cell line. In yet a further embodiment, the methods for producing a vaccine will comprise the steps of inoculating cells of a continuous animal cell line in a culture medium with the circular ssDNA virus thereby ensuring both that the medium of the continuous cell line comprises interferon and that endosomal-lysosomal system acidification in the continuous animal cell line is reduced. The methods according to this aspect of the invention further comprise the steps of allowing the ssDNA virus to replicate in the continuous animal cell line; and obtaining the circular ssDNA virus or components thereof from the continuous animal cell line or said medium.

In the methods according to this aspect of the invention, the step of ensuring that the medium of the continuous cell line comprises interferon is in particular embodiments ensured by adding an exogenous interferon to the medium of said continuous cell line or adding an agent which ensures the endogenous production of an interferon by the cell line; a further optional step comprises allowing said ssDNA virus to replicate in said continuous animal cell line; in further steps of the method of the present invention, the circular ssDNA virus or components thereof are isolated from the continuous cell line and/or the medium of the cell line and used in the development of a vaccine.

In the methods according to this aspect of the invention, the step of ensuring the reduction of endosomal/lysosomal system acidification of the continuous animal cell line is, in particular embodiments ensured by addition of lysosomotropic endosomal/lysosomal acidification inhibitors to the cultivation medium. Most particularly, lysosomotropic endosomal/lysosomal acidification inhibitors are used.

According to yet another aspect the invention provides in vitro methods for determining the infection of a animal or a cell culture by an animal circular ssDNA virus. Such methods involve increasing the amount of virus before detection. Different embodiments of this method are envisaged within the context of the invention. In a particular embodiment the amount of virus in the sample is increased before detection by using interferon. In other embodiments, this increase is ensured by ensuring that endosomal-lysosomal system acidification is reduced. In a further embodiment, the increase in virus titre is ensured by the combined use of interferon and reduction of endosomal-lysosomal system acidification.

According to one embodiment of this aspect of the invention, methods are provided whereby the amount of virus is directly increased in the sample (or a fraction thereof) of the animal or the culture. This method is particularly suited for samples of animals and cell cultures that comprise cells, more particularly comprising cells which are susceptible to infection by the circular ssDNA virus (such as, but not limited to blood or ascites samples or cell-comprising culture samples). Typically according to this embodiment, the method can comprise one or more steps comprising adding interferon or an agent capable of inducing interferon to a cell-containing sample (or a fraction thereof) of said animal or cell culture and/or reducing endosomal-lysosomal system acidification in the continuous animal cell line. The methods further comprise the steps of allowing the replication of the circular ssDNA virus in the sample, and detecting the presence of the circular ssDNA virus in the sample.

Alternatively, the amount of virus in the sample is increased indirectly, through the intermediate of a cell line susceptible to infection by the animal circular ssDNA virus. This method can also be used to detect the presence of circular ssDNA virus in a sample which does not comprise cells, more particularly does not comprise cells susceptible to infection by the circular ssDNA virus (eg. supernatant or serum). Typically, according to this embodiment, the method can comprise the steps of adding the sample (or fraction thereof) for which the detection is to be performed to a culture of cells susceptible to infection by circular ssDNA virus (or visa versa). The titre of the virus is then increased e.g. by adding interferon to the latter mixture (comprising the culture of susceptible cells and the sample) and/or endosomal-lysosomal system acidification inhibitors and detecting of the presence of ssDNA virus in the medium of the culture of cells. Alternatively, the susceptible cells are cells which produce interferon either naturally or as a result of genetic modification. Additionally or alternatively, the susceptible cells are cells in which the endosomal-lysosomal system acidification is reduced as a result of a selection and/or genetic modification.

In the above-described methods, detection of animal circular ssDNA virus is indicative of the infection of the sample by the animal circular ssDNA virus.

The above methods represent an improvement over current detection methods of circular ssDNA virus in animal and cell culture samples, as the sensitivity is increased. Thus the present invention provides improvements of viral detection methods whereby the increase in sensitivity of at least ×2 is observed, compared to detection in the absence of IFN and reduction of endosomal-lysosomal system acidification.

In particular embodiments of the methods of the present invention, the interferon used is IFN-alpha and/or IFN-gamma.

According to yet another aspect of the present invention, methods are provided to improve the immune response in an animal to a vaccine against an animal circular ssDNA virus. In particular embodiment these methods comprise administration of interferon to the animal, wherein the interferon ensures the improved immune response to said vaccine. In another embodiment, these methods comprise administration of endosomal-lysosomal system acidification inhibitors to the animal, resulting in an improved immune response.

Such methods can additionally comprise the step of administering a vaccine against an animal circular ssDNA virus to the animal, whereby the administration of interferon and/or endosomal-lysosomal system acidification inhibitors can occur sequentially to (shortly, most particularly within 24 hrs, before or after) or simultaneously with the administration of the vaccine. Such methods can optionally further comprise identifying an animal in need of such an improved immune response, either before or after administration of the vaccine thereto.

Thus the present invention provides the use of one or more interferons and/or endosomal-lysosomal system acidification inhibitors in the manufacture of a medicament for the improvement of the immune response to the vaccination with an attenuated animal circular ssDNA virus. A specific embodiment of the invention the animal circular ssDNA virus is a Circovirus.

According to this aspect of the invention, vaccines are provided comprising both an attenuated animal circular ssDNA virus and interferon and/or endosomal-lysosomal system acidification inhibitors. Alternatively, kits for vaccination are provided which comprise a) a composition comprising an attenuated animal circular ssDNA virus vaccine and b) an interferon and/or one or more endosomal-lysosomal system acidification inhibitors for simultaneous or sequential administration to an animal.

DETAILED DESCRIPTION OF THE INVENTION

The present invention relates to the in vitro cultivation of animal circular ssDNA viruses. The term "animal circular ssDNA virus" is used to refer to a subgroup of animal single strand DNA (ssDNA) viruses, which infect eukaryotic non-plant hosts, and which have a circular genome. Thus, the animal circular ssDNA viruses are to be distinguished from ssDNA viruses that infect prokaryotes (i.e. Microviridae and Inoviridae) and from ssDNA viruses that infect plants (i.e. Geminiviridae and Nanoviridae). At the same time they are to be distinguished from linear ssDNA viruses that infect non-plant eukaryotes (i.e. Parvoviridiae). In the present invention "non-plant" and "animal" will be used as synonyms, whereby "animal" will include human, unless specified as "non-human".

The group of circular animal ssDNA viruses encompasses both the Anelloviruses and the Circoviridae. Whether the taxonomic group of the Anelloviruses should be placed within or next to the group of Circoviridae has not yet been completely established. Anellovirus members are at present not yet included in the official classification of the ICTV (International Committee on Taxonomy of Viruses) [see Biagini (2004) *Vet. Microbiol.* 98, 95-2004].

The Circoviridae represents a taxonomic group which comprises both Circovirus and Gyrovirus. Examples of Circovirus are Psittacine Beak and Feather Disease Virus, Bovine circovirus, Canary circovirus, Columbid circovirus, Goose circovirus, Mulard duck circovirus, Muscovy duck circovirus, and Porcine circovirus (Porcine circovirus 1 (PCV-1) and Porcine circovirus 2 (PCV2)).

"PCV2" or Porcine circovirus 2, is a very small virus with a relatively simple structure. The circular ambisense 1.7 Kb genome codes for two major proteins. On the viral strand, open reading frame (ORF) 2 codes for the capsid protein and on the complementary strand, ORF1 codes for two non-structural proteins Rep and Rep' which form a complex that is involved in the replication of the genome. Besides these three viral proteins, no others have been characterised to this date. The fact that PCV2 does not code for a viral DNA-polymerase, makes it dependent of cellular enzymes to complete its infectious cycle. Many different strains, isolated from PMWS-affected pigs, healthy pigs or aborted foetuses have been characterized.

The taxonomic group of the Anellovirus comprises the SEN virus, the Sentinel virus, the TTV-like mini virus and the TT virus. Different types of TT virus have been described including TT virus genotype 6, TT virus group, TTV-like virus DXL1 and TTV-like virus DXL2.

In the context of the present invention, the term 'virus' (such as when referring to an animal circular ssDNA virus can be used to refer to either or both wild-type isolates and/or spontaneously or purposefully mutated laboratory strains. According to a particular embodiment, a virus is an attenuated virus.

The present invention relates to the cultivation of animal circular ssDNA virus in an animal cell line, especially a continuous cell line. The animal cell lines envisaged within the context of the present invention preferably encompass any cell line that can be passaged multiple times (e.g. at least 10 times) in vitro and which can be infected by a circular animal ssDNA virus. The suitability of a cell line for use in the context of the present invention can be investigated by assaying the presence of circular animal ssDNA viral proteins (immunostaining) or circular animal ssDNA viral DNA (hybridisation or PCR amplification) after infection of said cell line with an animal circular ssDNA virus. The term cell line in the context of the present invention encompasses both transfected and non-transfected cell lines.

Inoculation or infection of a susceptible animal cell line by an animal circular ssDNA virus can be achieved by routine methods. Typically inoculation is performed as described herein using a strain of circular ssDNA virus at a multiplicity of infection ranging from about 0.01 to about 1. The virus is usually diluted in MEM and inoculated on the cell cultures by incubating cells and virus for 1 hour at 37° C. After 1 hour, new culture medium is added.

A particular embodiment of the present invention relates to the cultivation of PCV2 in continuous animal cell lines in vitro. According to one embodiment of the invention, the cell lines are porcine cell lines. PCV2 is able to replicate in most porcine cell lines in vitro. Most particularly, the cell lines envisaged in the context of the present invention are immortalised porcine cell lines such as, but not limited to the porcine kidney epithelial cell lines PK-15 and SK, the monomyeloid cell line 3D4/31 and the testicular cell line ST. PCV2 is also able to replicate to a lesser extent in CHO cells (Chinese hamster ovaries). A number of non-porcine cell lines are resistant to PCV2-infection: MARC-145, MDBK, RK-13, EEL). Additionally or alternatively, particular embodiments of the methods of the invention make use of an animal cell line which is an epithelial cell line, i.e. a cell line of cells of epithelial Another embodiment of the present invention relates to the cultivation of TTvirus in animal cell lines in vitro. In the context of this embodiment continuous cell lines susceptible to infection with TTvirus are envisaged. Such cells lines can be, but are not limited to cell lines of human or primate origin, such as human or primate kidney carcinoma cell lines.

A particular embodiment of the present invention relates to the cultivation of PCV2 in continuous animal cell lines, for the production of vaccines, more particularly vaccines for use in pigs. When referring to "Pigs" in the context of the present invention, reference is made to a member of the Suidae, more particularly, any race or strain of *Sus scrofa domestica*. It includes free living and domesticated pigs. It also includes to pigs, which underwent a special regimen such as SPF (Specific Pathogen Free) pigs, or gnotobiotic pigs (gnotobiotic piglets (caesarian-derived, colostrum-deprived, raised in a germ-free environment).

The present invention refers to a method for the in vitro cultivation of an animal circular ssDNA virus. According to a particular embodiment the circular ssDNA virus is a member of the Circoviridae or is an Annelovirus. In a particular embodiment of the present invention, the circular ssDNA virus is a Circovirus, most particularly PCV2. More particularly, the method of the invention is demonstrated for the cultivation of PCV2 strain Stoon-1010. This strain was isolated from the first described case of PMWS and can therefore be considered to be the reference strain.

According to a first aspect of the present invention improved cultivation of the circular ssDNA virus (i.e. increased virus titre) is obtained in vitro by infection of a continuous animal cell line with the circular ssDNA virus in the presence of an interferon. Interferons useful in the context of the present invention include Type I and Type II interferons. According to a particular embodiment of the present invention, IFN-gamma is used. Apart from wild type interferons (isolated from mammalian or bacterial cells or recombinant), the invention can also be performed with modified versions (mutated and/or truncated versions) of an interferon, as long as the IFN remains active in one of the bioassays known to the skilled person, such as, but not limited to the one described herein for IFN-alpha.

According to a particular embodiment of the invention the method encompasses the addition of one or more exogenous interferons to the cell culture. The term 'exogenous' in this context means that the interferon(s) is(are) not produced by the cell line itself but added directly or indirectly to the medium.

The concentration of interferons added to the culture of animal circular ssDNA viruses according to the present invention is a concentration of at least 2 U/ml, particularly at least 50 U/ml, more particularly at least 100 U/ml. Typical concentrations of IFN-gamma added to large scale production units will be around 250-500 U/ml, but most likely even higher concentrations will further increase virus titres.

The addition of exogenous interferons can be achieved in different ways. According to a particular embodiment of the invention, the cytokine is added in purified form, e.g. from a cytokine stock as described above. Alternatively, however, the interferon can be present in a medium, e.g. as obtained from a cell culture which produces interferon. Typically, immunological cells are capable of producing interferons when stimulated. An exemplary source of IFN may be the medium of PBMCs, or of any specific cell type producing a type of IFN such as but not limited to leukocytes, fibroblasts, epithelial cells, macrophages, lymphocytes, plasmacytoid dendritic cells, and bacterial cells. Compounds which are known to induce IFN production in certain cell types and which can be used in the context of the present invention include, but are not limited to concanavalin A, 12-O-tetradecanoyl-phorbol-13-acetate, IL-2, Poly I:C. Alternatively, interferon production can be induced in a number of cell types by infection with a micro-organism or foreign agent, e.g. of viral, bacterial or parasitic origin or contacting the cells with non-infectious proteins. Methods to induce IFN production in cultures by viruses have been described, e.g. in U.S. Pat. No. 3,951,740. Such a virus can be a second animal virus, such as porcine reproductive and respiratory syndrome virus (PRRSV) or porcine parvovirus (PPV). Alternatively, e.g. in the case of human cells, the other virus can be an animal virus such as Hepatitis C virus or HIV.

According to a further embodiment of the present invention the method for cultivating animal circular ssDNA virus encompasses ensuring the production of interferons by the cell line itself, i.e. the production of endogenous interferons.

A limited number of continuous cell lines are capable of producing interferons, such as, but not limited to lymphoblastoid cell lines (e.g. Namalva cell lines producing "Namalva interferon"). Most continuous animal cell lines however do not naturally produce interferons. Nevertheless, the present invention also envisages cell lines capable of producing interferon as a result of transfection. Cell lines capable of producing IFN as a result of genetic manipulation are generally referred to herein as transgenic cell lines. Such a production of one or more interferons by transfected cell lines can be either constitutive or inducible. Methods of transfecting cell lines suitable in the context of the present invention, such as, but not limited to the PK15 cell line, are known in the art. The cloning and expression of porcine interferon alpha and gamma is described in Xia et al (2005) Vet Immunol Immunopathol. 104, 81-89. Alternatively, a wide variety of vectors for the recombinant expression of genes in eukaryotic cells are available from e.g. Clontech, InVitrogen, Stratagene. DNA sequences encoding porcine interferon gamma [NM_213948] and interferon alpha [NM_214393] are deposited in Genbank.

Protocols for the transfection of cell are described in e.g. Cell Biology: A Laboratory Handbook (1998) Ed. J. Celis, Academic Press, or are available from the manufacturers of transfecting agents (eg Fugene (Roche Diagnostics) or electroporation apparatus (e.g. BioRad).

According to this aspect of the invention endogenous production of interferon by the cell line is ensured by transfection of the cell line and, in the case of inducible promoters, induction of the inducible interferon production by a compound which is capable of activating the inducible promoter.

The amount of interferon used or observed in the context of the present invention will be referred to as a concentration (i.e. amount/ml). A concentration can be expressed in weight (mg/ml) or molarity (M) or by activity (Units/ml).

Assays for determining activity in Units/ml are known in the art. As there is no standard for porcine interferon, the units of porcine interferons are usually determined with respect to the international reference standard for the corresponding human interferon. For instance the units of porcine interferon alpha is determined with respect to the activity of human leukocyte interferon (Ga23-902-530) provided by the National Institutes of Health [see Pestka, S. (1986) Methods in Enzymology 119, 14-23]. The activity of porcine IFN-alpha can be determined using the cytopathic effect inhibition assay as described by Rubinstein et al S. [(1981) J. Virol. 37, 755-758] and Famillett et al. [(1981) Methods in Enzymology 78, 387-394]. In such an antiviral assay about 1 unit/ml of interferon is the quantity necessary to produce a cytopathic effect of 50%.

In the context of the present invention, interferon concentrations will refer to the exogenously added interferon as calculated over the amount of cell culture medium. Alternatively, when IFN is produced endogenously by the cell line according to a particular embodiment of the invention, IFN concentrations in the medium will reflect the amount of interferon produced by the cells which are present in the cell culture medium. The activity and concentration of interferon(s) can be assayed by quantitative measurements (e.g. ELISA) or by qualitative measurements (bioassays).

Thus, typically the medium of the continuous cell lines used to produce animal circular ssDNA viruses according to the present invention will contain one or more interferons at a concentration of at least 2 U/ml, more particularly at least 20 U/ml, even more particularly at least 100 U/ml, most particularly 500 U/ml or more.

Where the interferon is exogenously added or endogenous production can be controlled (e.g. use of an inducible promoter), according to particular embodiments of the methods of the present invention, the time periods envisaged for contacting the cells with interferon will be between 30 minutes and 48 hrs or more. It will be understood that the time period is determined at least in part by the concentration of IFN used or envisaged to be produced by the cells. More particularly, a time period of 24 hrs incubation in the presence of 100-500 U/ml interferon is envisaged.

According to another aspect of the invention, improved cultivation of the circular ssDNA virus (i.e. increased virus titre) is obtained in vitro by infection of a continuous animal cell line with the circular ssDNA virus and inhibiting (with the aim of at least reducing) endosomal-lysosomal system acidification in the cells. The endosomal-lysosomal system consists of membrane bound organelles that functions in the cellular housekeeping by internalization, sorting, and breakdown of macromolecules (Mellman, I. 1996. Annu. Rev. Cell Dev. Biol. 12, 575-625). The endosomal-lysosomal system is composed of primary endocytic vesicles, early endosomes, late endosomes, and lysosomes. The endosomal-lysosomal system is characterized by gradual acidification of its vesicles as they mature from early endosomes into lysosomes. It has been found that reduction of endosomal-lysosomal system acidification increases susceptibility of certain cells to PCV2 infection.

Accordingly, the present invention envisages methods whereby endosomal-lysosomal system acidification is reduced or inhibited. Endosomal-lysosomal system acidification can be inhibited by lysosomotropic agents. The term 'lysosomotropic' as used herein designates all substances that are taken up selectively into lysosomes irrespective of their chemical structure or mechanism of uptake (De Duve et al., 1974. Biochem. Pharmacol. 23:2495-2531). The pH of endosomal and/or lysosomal vesicles can be measured by methods known to the skilled person (such as, but not limited to described inter alia by Maxfield et al. 1982, J. Cell Biol. Vol 95:676-681; Ohkuma and Poole 1987, Proc. Natl Acad Sci USA 75:3327-3331). In particular embodiments the reduction of acidification envisaged corresponds to an increase of pH of at least 0.5 units, more particularly 1 unit or more.

According to one embodiment, a lysosomotropic agent is used, more particularly a lysosomotropic acidification-inhibiting agent, i.e. a lysosomotropic agent capable of changing the acidic pH of the lysosomes and/or other vesicles within the endosomal-lysosomal system. Lysosomotropic agents, such as chloroquine diphosphate, ammonium chloride and monensin raise pH within lysosomes, thereby also resulting in an increased pH. It has been found in the present invention that reduction of endosomal-lysosomal system acidification by treatment of cells with lysosomotropic agents capable of raising the pH within the endosomal-lysosomal system increases the susceptibility of cells to PCV2 infection. Particularly, suitable lysosomotropic agents for use in the methods of the present invention thus include, but are not limited to, ammonium chloride, chloroquine diphosphate and monensin.

Further examples of suitable inhibitors of endosomal-lysosomal acidification include tamoxifen (Nihal et al., 1999. Proc Natl Acad Sci USA 96(8):4432-7), bafilomycins and concanamycins (Drose & Altendorf. 1997. J. Exp. Biol. 200: 1-8), nigericin, N-(3-[(2,4-dinitrophenyl)-amino]-propyl)-N-(3-aminopropyl-methylamine)dihydrochloride (DAMP) (Anderson et al., 1984. Proc Natl Acad Sci USA 81:4838-4842), primaquine (DeDuve et al., 1974. Biochem Pharmacol 23:2495-2531), methylamine, Destruxin B (Muori et al., 1994. Biochem Biophys Res Commun 205:1358-1365).

According to another embodiment, endosomal acidification is reduced or inhibited by other means, such as, but not limited to, exposure to cadmium or pyocyanin (produced by

*Pseudomonas aeruginosa*) or other agents that directly inhibit V-type H+-ATPase (proton pump; V-ATPase), e.g. bafilomycins and concanamycins, and/or inhibit intracellular vesicle trafficking within the endosomal-lysosomal system; specific antibiotics such as duramycin and azithromycin capable of inhibiting acidification of the endosomal-lysosomal system; Amphotericin B, an antifungal drug, which blocks the fusion between endosomes and/or the fusion between endosomes and lysosomes; infection with *Rhodococcus equi* and *Francisella tularensis*, bacteria that have been described to survive a phagolysosomal environment by suppressing acidification of the phagolysosome (Clemens et al., 2004. Infect Immun. 72:3204-17; Toyooka et al., 2005. J Med Microbiol. 54:1007-15.); finally the infection of cell lines carrying genetic modifications resulting in loss of function of proteins involved in endosome acidification machinery is also envisaged, including cell lines which naturally or via selection have defective endosome acidification (such as CHO mutants DTG 1-5-4 and DTF 1-5-1 (Robbins et al. 1983, J. Cell Biol. 99:1296-1308)).

Accordingly, according to this aspect of the invention, methods are provided for the in vitro cultivation of an animal circular ssDNA virus comprising the step of inoculating cells of a continuous animal cell line in a culture medium with said circular ssDNA virus, while inhibiting endosomal-lysosomal acidification. In a particular embodiment, the reduction of endosomal-lysosomal acidification is ensured by cultivating the cells in the presence of a pH stabilizing agent. More particularly, the pH stabilizing agent is a lysosomotropic agent capable of inhibiting acidification within lysosomes.

Where a stabilizing agent is used according to the methods of the present invention, incubation of the continuous cell line with the stabilizing agent can be performed prior to, simultaneously with, or subsequent to PCV2 inoculation of the cells. According to a particular embodiment, the cells are treated with one or more stabilizing agents after PCV2 inoculation.

The amount of stabilizing agent used in the methods of the invention is determined by the nature and characteristics of the agent used. Where the use of lysosomotropic agents is envisaged, the amount of agent is typically between 0.1 μM and 200 mM. The present invention demonstrates that significant enhancement of PCV2 infection can be obtained by using 25 mM ammonium chloride, 125 μM chloroquine diphosphate and/or 6 μM monensin. Typically incubation with stabilizing agents takes place for a period between 30 min and 2-5 days. Most particularly an incubation time of 24 hrs with the agents of the invention is envisaged.

Where other methods of inhibiting endosomal-lysosomal system acidification are used, other concentrations and/or time periods of incubation may be appropriate. These can be easily optimized by the skilled person by optimization experiments as performed for the lysosomotropic agents described herein.

According to a further aspect of the invention, improved cultivation of the circular ssDNA virus (i.e. increased virus titre) is obtained in vitro by infection of a continuous animal cell line with the circular ssDNA virus in the presence of an interferon and reduction of endosomal-lysosomal system acidification in the cells. According to this aspect, the effect of endosomal-lysosomal system acidification reduction and the presence of an interferon on the susceptibility of cells to PCV2 infection is combined. More particularly the combined use of endosomal-lysosomal system acidification inhibitors and IFN generates a synergistic effect on PCV2 production.

Accordingly, according to this aspect of the invention, methods are provided for the in vitro cultivation of an animal circular ssDNA virus comprising the step of inoculating cells of a continuous animal cell line in a culture medium with said circular ssDNA virus, in the presence of interferon, as described hereinabove, and cultivating the continuous animal cell line while inhibiting endosomal-lysosomal system acidification. Generally, the methods according to this aspect of the invention involve a combination of the methods of cultivation in the presence of IFN and the methods of cultivation whereby endosomal-lysosomal system acidification is inhibited as described in the sections above. According to one embodiment the addition of interferon and the reduction of endosomal-lysosomal system acidification is performed simultaneously. Alternatively, the addition of interferon and the reduction of endosomal-lysosomal system acidification can be performed in subsequent steps, either in the same medium or with intermediate removal of the cultivation medium. According to a particular embodiment of the present invention, the cells are contacted with interferon prior to the inoculation with PCV2, whereafter the cultivation medium is changed and an agent ensuring inhibition of endosomal acidification is added to the new medium (with or without interferon) for further cultivation. Where presence of IFN is ensured by endogenous production of IFN by the cells, endosomal acidification inhibitors can be added prior to or shortly after inoculation of the cells with PCV2.

According to one aspect, the present invention provides methods for the cultivation of viruses, whereby increased virus titres are obtained, which is of interest e.g. in the production of vaccines. The average titre of virus in a medium of infected cells is between 3.4 and 4.5 $\log_{10}$ $TCID_{50}$/ml. Using the methods of the present invention, the concentration of an animal circular ssDNA virus in an undiluted culture medium, can raise up to a titre of 4.8 to 5.7 $\log_{10}$ $TCID_{50}$/ml or more. Thus, the present invention relates to an improvement of the cultivation of animal circular ssDNA virus which ensures an increase in titre of approximately 1.3 $\log_{10}$ TCID50/ml or more. It is demonstrated herein that using the methods of the invention, titres corresponding to titres representative of industrial production can be obtained.

The production of virus-containing cell cultures according to the present invention can be carried out in different scales, such as in flasks, roller bottles or bioreactors. The media used for the cultivation of the cells to be infected are known to the skilled person and will comprise the standard nutrients required for cell viability but may also comprise additional nutrients dependent on the cell type. Optionally, the medium can be protein-free. Depending on the cell type the cells can be cultured in suspension or on a substrate.

Thus, one aspect of the invention relates to circular animal ssDNA virus, which can be isolated from a medium and/or infected cells after cultivation according to the present invention. The isolated virus can be used to obtain one or more of the viral proteins or to isolate the viral DNA therefrom.

The purification and isolation of circular animal ssDNA virus is known by the skilled person and is described for example by Meehan et al. (1998) *J. Gen. Virol.* 79, 2171-2179. Protection of swine against post-weaning multi-systemic wasting syndrome by PCV2 proteins has been demonstrated (Blanchard et al. (2003) *Vaccine* 21, 4565-4575).

Alternatively, the isolated virus can be used as such in the production of an attenuated or inactivated virus for vaccination. Attenuation of virus strains for use in vaccination is performed by different methods, including repeated passaging on cells, particularly on cell lines, such as PK/15 or by activation of virus-associated endonuclease (Schodeller et al. J. Gen. Virol., 65, 1567-1573). Inactivation of a virus can be achieved by using chemical methods, e.g. by exposing the antigen to a chemical agent such as formaldehyde (formalin), paraformaldehyde, beta.-propiolactone or ethyleneimine or its derivatives (Larghi et al. (1980) *J. Clin Microbiol* 11, 120-122); US patent application 2002/0146432), or by UV-irradiation.

Thus, one aspect of the present invention relates to a method for the preparation of a vaccine against a circular animal ssDNA virus, which encompasses the cultivation of the virus in accordance with the methods of the present invention. A vaccine according to the present invention can comprise either an immunogenic agent or a compound which, upon introduction into the host, ensures the production of an immunogenic agent. Thus a vaccine can comprise DNA, RNA, or protein material, or both, including the complete virus.

In a particular embodiment the vaccine is a vaccine for the prevention of postweaning multisystemic wasting syndrome (PMWS) in pigs caused by PCV2 strains such as strain Stoon-1010. In another particular embodiment the vaccine is a vaccine for the prevention of the abortion of pigs caused by the abortion-associated PCV2 strain 1121. In another particular embodiment the vaccine is a vaccine for the prevention of hepatitis-like disorders caused by Anelloviruses such as TT virus.

Besides the immunogenic agent or the compound which ensures the production of the immunogenic agent in vivo, vaccines generally comprise a vehicle or diluent acceptable from the veterinary point of view, optionally an adjuvant acceptable from the veterinary point of view, as well as optionally a freeze-drying stabilizer. When comprising attenuated virus particles, vaccines will generally comprise from $10^{3.0}$ to $10^{6.0}$ TCID50 (50% tissue culture infective dose). Inactivated vaccines can be supplemented with adjuvant, advantageously by being provided in the form of emulsions, for example water-in-oil or oil-in-water, according to techniques well known to persons skilled in the art. It will be possible for the adjuvant character to also come from the incorporation of a customary adjuvant compound into the active ingredient. Among the adjuvants which may be used, there may be mentioned by way of example aluminium hydroxide, the saponines (e.g. Quillaja saponin or Quil A; see Vaccine Design, The Subunit and Adjuvant Approach, 1995, edited by Michael F. Powel and Mark J. Newman, Plennum Press, New-York and London, p. 210), Avridine® (Vaccine Design p. 148), DDA (Dimethyldioctadecyl-ammonium bromide, Vaccine Design p. 157), Polyphosphazene (Vaccine Design p. 204), or alternatively oil-in-water emulsions based on mineral oil, squalene (e.g. SPT emulsion, Vaccine Design p. 147), squalene (e.g. MF59, Vaccine Design p. 183), or water-in-oil emulsions based on metabolizable oil (preferably according to WO-A-94 20071) as well as the emulsions described in U.S. Pat. No. 5,422,109 or those described in WO-A-9416681. It is also possible to choose combinations of adjuvants, for example Avridine® or DDA combined with an emulsion. As freeze-drying stabilizer, there may be mentioned by way of example SPGA (Bovarnik et al., *J. Bacteriology* 59, 509), carbohydrates such as sorbitol, mannitol, starch, sucrose, dextran or glucose, proteins such as albumin or casein, derivatives of these compounds, or buffers such as alkali metal phosphates.

Another aspect of the present invention relates to the provision of a method for diagnosing an infection of animal circular ssDNA virus in a sample, whereby the sensitivity of the detection is increased. These methods are of interest in the detection of postweaning multisystemic wasting syndrome (PMWS) or susceptibility thereto, as pigs with high PCV2 replication have been shown to be more likely to develop PMWS than pigs with low PCV2 replication (Segalés and Domingo, 2002, Vet Q. 2002 September; 24(3):109-24). The sample used in the detection methods according to this aspect of the present invention. Such a sample can be either a cell-containing sample (which as used herein refers to a sample comprising cells which are susceptible to animal circular ssDNA virus) or a sample which itself does not comprise cells which are susceptible to infection with circular ssDNA virus (e.g. supernatant of a cell culture). Typically, the sample will be either a cell-containing or non cell-containing sample of an animal or a cell culture. The detection can either be performed on the sample or on a fraction thereof, but for simplification purposes the methods of the invention will generally refer to the sample. The increase in sensitivity of detection is obtained by increasing the amount of virus before detection using interferon and/or inhibiting endosomal-lysosomal system acidification as described herein. This increase in amount of virus can be achieved in the sample directly, whereby detection of the ssDNA virus can also be performed on the sample directly. Alternatively, the increase in amount of virus is achieved after addition of the sample to a cell culture susceptible to animal circular ssDNA virus infection and ensuring the medium of the cell culture contains or is contacted with interferon and/or conditions inhibiting endosomal/lysosomal system acidification. This can be ensured by addition of interferon or an interferon inducing agent to the medium of the cell culture or by ensuring that the cell culture endogenously produces interferon. Additionally or alternatively, this is ensured by addition of one or more endosomal/lysosomal acidification inhibitors to the cell culture or by ensuring that the cell culture endogenously generates an increased pH in the lysosomes or other organelles within the endosomal-lysosomal system (e.g. as a result of genetic modification of a gene involved in endosomal/lysosomal acidification). When a cell culture susceptible to animal circular ssDNA virus infection is used, detection of the presence of ssDNA virus is performed on the cells or the medium of the cell culture.

Thus, according to a first embodiment of this aspect of the invention, the sample is e.g. a cell-comprising sample of an animal, such as a blood sample. Addition of an IFN, or an agent capable of inducing IFN production (by the cells in the sample) to the sample of the animal, is used to obtain an increase in virus-titre in the sample such that the sensitivity of the detection of the circular ssDNA virus in the sample is increased. Agents capable of inducing IFN in e.g. blood cells are described herein. Additionally or alternatively, addition of an agent capable of inhibiting endosomal/lysosomal acidification or an agent which indirectly ensures reduction of acidification in the endosomal-lysosomal system is used to ensure in an increase in virus-titre in the sample, similarly resulting in an increased sensitivity of detection. Where both interferon and reduction of endosomal/lysosomal acidification are used, a synergistic effect on sensitivity is obtained.

According to another embodiment of this aspect of the invention, the sample (which can be a sample which does not contain cells, such as serum or cell culture supernatant) is contacted with a cell culture which is susceptible to infection by a circular ssDNA virus, to which the interferon and/or agent inhibiting endosomal/lysosomal acidification is then added. Alternatively, the production of interferon by the cell culture used can be ensured, either by selecting an appropriate IFN producing cell line or by genetic modification of a susceptible cell line. Similarly, a cell line with altered acidification of the endosomal/lysosomal system can be used. Detection of the circular ssDNA virus is performed on the medium or the cells of the cell culture. Such a detection can be performed both qualitatively and/or quantitatively based on the detection of the presence of viral DNA, viral proteins or the detection of infectious virus. Again, cultivation according to the methods of the invention will induce a higher virus titre such that the sensitivity of the detection is increased. According to this aspect of the invention the cell cultures susceptible to animal circular ssDNA virus infection can be a continuous cell line or can be a primary cell culture such as a culture of PBML's.

According to yet another aspect of the invention interferon and/or inhibitors of endosomal-lysosomal system acidification are used to mediate the response of animals, more specifically pigs or humans to the vaccination with an attenuated circular ssDNA virus. Attenuated viruses are modified viruses which still replicate in the host but are no longer (or less) virulent, and can be obtained as described herein. According to this aspect interferon and/or inhibitors of endosomal-lysosomal system acidification are used to increase the replication of attenuated PCV2 in vivo and thus to enhance the immune response to the virus upon administration to an animal. Administration of the interferon and/or inhibitors of endosomal-lysosomal system acidification to the animal can be done separately (i.e. before, during or after administration of the virus vaccine) or together with the virus. Thus one aspect of the invention relates to a vaccine comprising both an animal circular ssDNA virus and interferon and/or inhibitors of endosomal-lysosomal system acidification.

BRIEF DESCRIPTION OF THE DRAWINGS

The following Examples, not intended to limit the invention to specific embodiments described, may be understood in conjunction with the accompanying Figures.

Black bar: effect of cytokines administered before inoculation; grey bar: during inoculation; white bar: post inoculation. All results represent the mean of three independent experiments+standard error of the mean.

Figure 2:
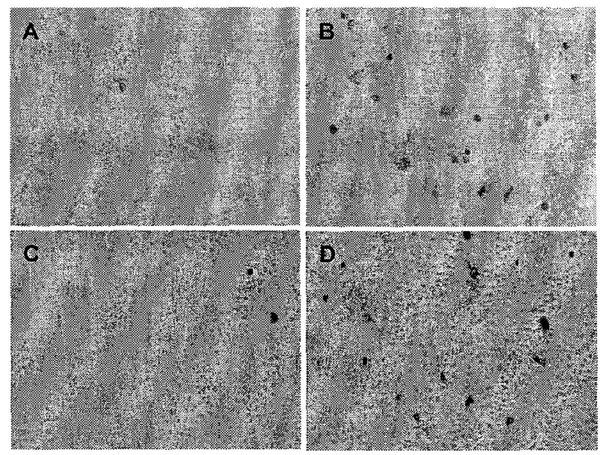

FIG. 2. Light microscopic pictures of the influence of IFN-gamma treatment on the number of PCV2 positive cells in PK-15 and 3D4/31 cells according to one embodiment of the invention. Pictures A and C show the number of PCV2 positive cells in respectively PK-15 and 3D4/31 cells. Pictures B and D show the number of PCV2 positive cells in respectively PK-15 and 3D4/31 cells treated with 500 U/ml IFN-gamma respectively after and before inoculation. All pictures are taken at a magnification of 100×.

Figure 3:
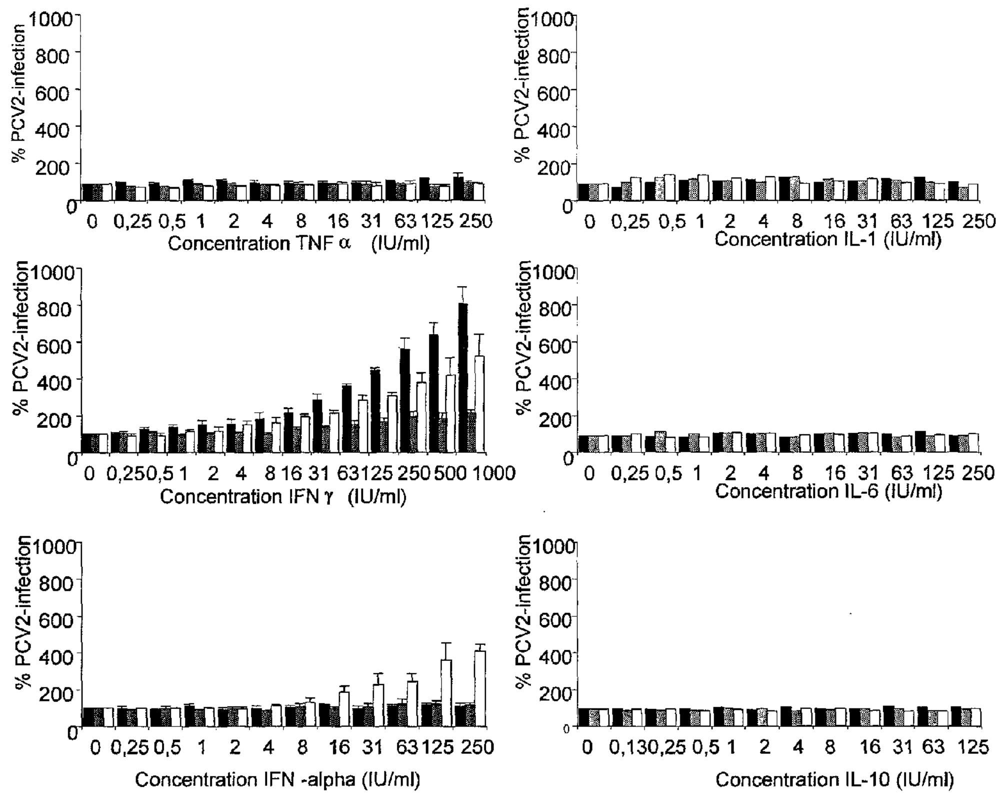

FIG. 3. Influence of cytokines on number of PCV2-infected 3D4/31 cells according to one embodiment of the invention.

Black bar: effect of cytokines administered before inoculation; grey bar: during inoculation; white bar: post inoculation. All results represent the mean of three independent experiments+standard error of the mean.

Figure 4:
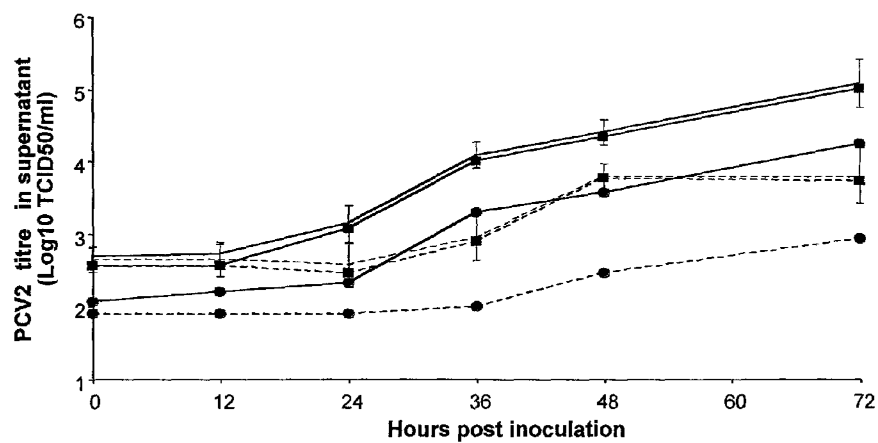

FIG. 4. Progeny virus production in PK-15 cells treated with 500 U/ml IFNγ compared to non-treated cells according to one embodiment of the invention. Full lines represent the titres obtained in PCV2-inoculated PK-15 cultures supplemented with 500 U IFN-γ per ml. Dashed lines represent titres obtained in PK-15 cultures without IFN-γ. Lines with black circles represent extracellular virus titres, lines with black cubes represent intracellular titres. Lines without symbols represent total PCV2 titres±standard error of the mean.

Figure 5:
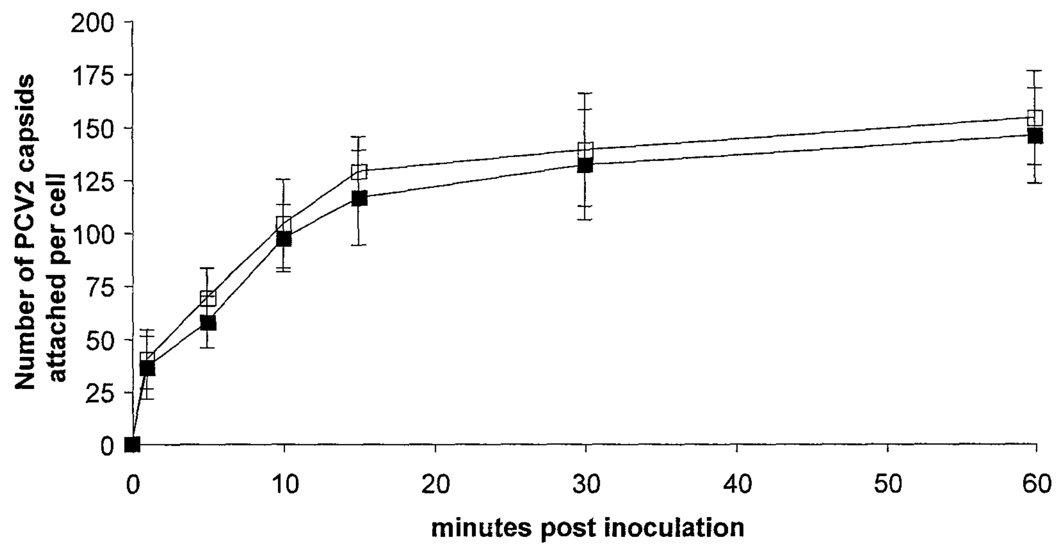

FIG. 5. Effect of interferon-gamma on attachment of recombinant PCV2-capsid virion-like particles to 3D4/31 cells according to one embodiment of the invention.

Black blocks represent the number of virion-like particles attached at different time points after inoculation tot non-treated 3D4/31 cells. White blocks represent the results obtained in 3D4/31 cells treated with 500 l/ml IFN-gamma during incubation of the virion-like particles with the cells. The results represent the average number of virion-like particle attached to 10 different cells±standard deviation.

Figure 6:
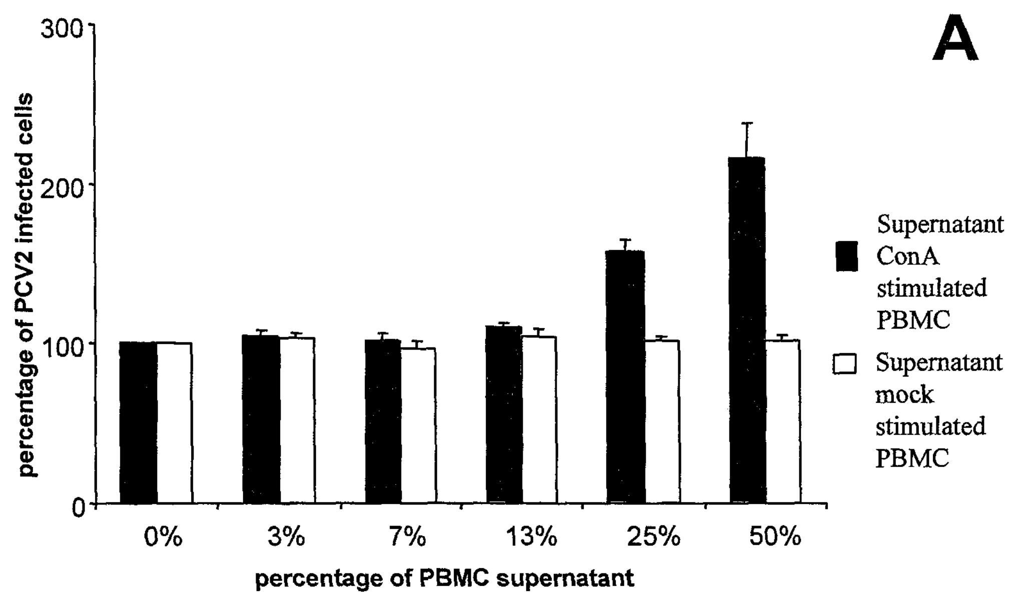

FIG. 6. Effect of naturally induced interferons on PCV2-infection in PK-15 cells according to one embodiment of the invention; Effect of BAL-fluids of PRCV and mock-inoculated pigs (A) and supernatant of ConA and mock-stimulated PBMC's (B) on the number of PCV2-infected PK-15 cells.

FIG. 7. Effect of endosomal-lysosomal system acidification inhibitors and/or IFN-gamma on the number of PCV2-infected PK-15 cells. PK-15 cells were pre-treated with (black bars) or without IFN-gamma (white bars) for 24 hours before they were inoculated with the same dose of PCV2. After PCV2 inoculation, cells were treated with (ammonium chloride, chloroquine diphosphate and/or monensin) or without (control) endosomal-lysosomal system acidification inhibitors for 24 hours. The number of PCV2-infected cells in all treatment combinations was counted after 36 hours incubation and compared with the number of PCV2-infected cells in non-treated cells.

Figure 8:
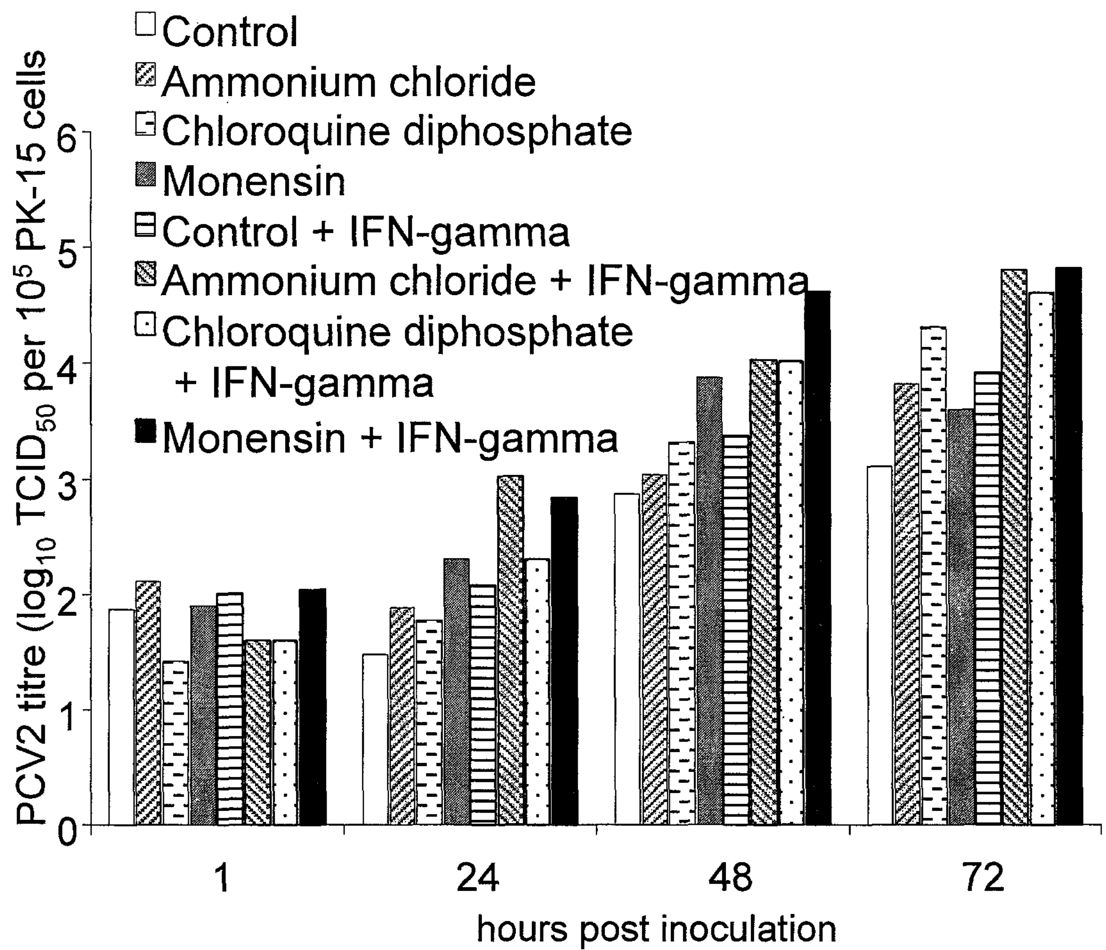

FIG. 8. Total PCV2 virus titres in PK-15 cells treated with IFN-gamma and/or inhibitors of endosomal-lysosomal system acidification; 25 mM ammonium chloride, 125 μM chloroquine diphosphate and/or 6 μM monensin.

EXAMPLES

General Methodology

Cells, Virus and Inoculation

PK/15 is a pig kidney epithelial cell culture derived from embryonic pigs, which is known to be uncontaminated with the porcine circovirus (PCV), pestiviruses, porcine adenoviruses and porcine parvoviruses [Allan G. et al. (1995) *Vet. Microbiol.* 44, 49-64].

PK-15 cells were seeded and maintained in culture medium containing 5%-10% fetal bovine serum (FBS), 0.3 mg/ml glutamine, 100 U/ml penicillin, 0.1 mg/ml streptomycin, 0.1 mg/ml kanamycin dissolved in minimal essential medium (MEM) (Gibco BRL®, Grand Island, USA) or dissolved in RPMI-1640 (GIBCO BRL®, Grand Island, USA) containing 1% nonessential amino acids (100×; GIBCO BRL®, Grand Island, USA) and 1 mM sodium pyruvate (GIBCO BRL®, Grand Island, USA). Cells were seeded at a concentration of 150,000 cells per ml of medium. For the detection of total viral antigen positive cells, the cells were seeded in 96-well microtiter plates (Nunc) (15,000-20,000 cells per well). To detect the expression of specific viral antigens, cells were seeded on sterile cover slips in Leighton tubes (150,000 cells per tube) and finally progeny virus production assays were performed in 24-well plates containing 15,000 cells per well.

In order to use cells, more related to the target cells in vivo, the monocytic cell line 3D4/31 was used to confirm the effect of the different cytokines on the number of PCV2-infected cells. The 3D4/31 cell line is a porcine monomyeloid cell lines that was established following transfection of primary porcine alveolar macrophage cultures with plasmid pSV3neo, carrying genes for neomycin resistance and SV40 large T antigen. (Weingartl et al. (2002) *J Virol Methods.* 10, 203-216). These cells were maintained in a 1:1 mixture of RPMI-1640 (Invitrogen) and DMEM (Invitrogen) supplemented with 10% fetal bovine serum, 0.3 mg/ml glutamine, 100 U/ml penicillin, 0.1 mg/ml streptomycin, 0.1 mg/ml kanamycin and 1% non-essential amino acids 100× (GIBCO BRL®, Grand Island, USA). These experiments were also performed in 96-well plates containing the same number of cells. Furthermore, to monitor the effect of IFN-gamma on the entry of PCV2 virion-like particles was determined, 3D4/31 cells were seeded at $2\times10^5$ cells/ml of medium onto microscopic slides mounted with an 8 well cell culture silicone chamber (Vivascience AG, Hanover). In all inoculations, the same PCV2-strain (Stoon-1010) was used at a multiplicity of infection of 0.01. The virus was diluted in MEM and inoculated on the cell cultures by incubating cells and virus for 1 hour at 37° C. After 1 hour, the inoculum was removed, the cultures were washed twice with MEM and new culture medium was added.

Cytokines and Neutralizing Antibodies

Porcine interleukin 1 (IL-1), interleukin 6 (IL-6), interleukin 10 (IL-10), and interferon gamma (IFN-gamma) were all purchased from the same company (R&D systems). The activity of the preparations is indicated on the leaflets supplied with the product. In case of IFN-gamma the activity is measured in an anti-viral assay using porcine PK-15 cells infected with EMC virus. The ED50 for this effect is typically 0.015-0.045 ng/mL.

Porcine recombinant interferon alpha (IFN-alpha) was kindly provided by Dr. Charley [Lefebvre F. et al. (1990) *J Gen Virol.* 71, 1057-1063]. Tumour necrosis factor alpha (TNF-alpha) was produced in L929 cells transfected with the pBMGNeo expression-vector containing the TNFα coding cDNA (Von Niederhausern et al. (1993) *Vet Immunol Immunopathol,* 38, 57-73). IL-1, IL-6, IL-10 and IFN-gamma were dissolved according to the manufacturers' instructions in lipopolysaccharide free phosphate buffered saline (PBS) supplemented with 0.1% bovine serum albumin (Sigma, Bornem, Belgium) to a concentration of 10 μg/ml. Subsequently, the cytokines were diluted in MEM supplemented with 10% FBS to a concentration eight times higher than the highest final concentration used in the assays.

IFN-alpha neutralizing antibodies (K9) were kindly provided by Dr. Charley.

Statistical Analysis

All experiments were repeated three times independently. The results presented herein represent the mean value obtained from these tree experiments. The variation between different experiments is represented by the standard error of the mean (SEM). Differences were considered to be significant when $p<0.05$. (p-value calculated with the Mann-Whitney test).

Example 1

Influence of Cytokines on the Total Number of PCV2-Infected Cells

The influence of the cytokines on the infection of PCV2 in PK-15 and 3D4/31 cells was determined by adding two-fold-dilution series of the cytokines to the medium of the cells before, during or after the inoculation. IL-1, IL-6, IL-10 and IFN-alpha were used in concentrations ranging from 0.25-250 Units/ml (U/ml), IFN-gamma was used in concentrations ranging from 0.25-1000 U/ml and IL-10 was used in concentrations from 0.13-125 U/ml. Cell cultures were either pretreated with the cytokines for 24 hours before inoculation, treated during the inoculation or the cytokines were added in the medium after the inoculation. After 36 hours of incubation at 37° C. in an environment supplemented with 5% CO2, the cells were fixed by drying and frozen at −20° C. The plates were stained with an immuno-peroxydase monolayer assay (IPMA) as described by Sanchez et al. (2003, *Vet Microbiol* 95, 15-25) and the number of PCV2-positive cells was counted by light microscopy. In each plate a control was inoculated with an equal dose of mock-treated PCV2 (treated with MEM without cytokines). The number of infected cells in this well was used as the reference and all results were expressed as a ratio to this reference.

Influence of Cytokines on the Total Number of PCV2-Infected PK-15 Cells

Figure 1:
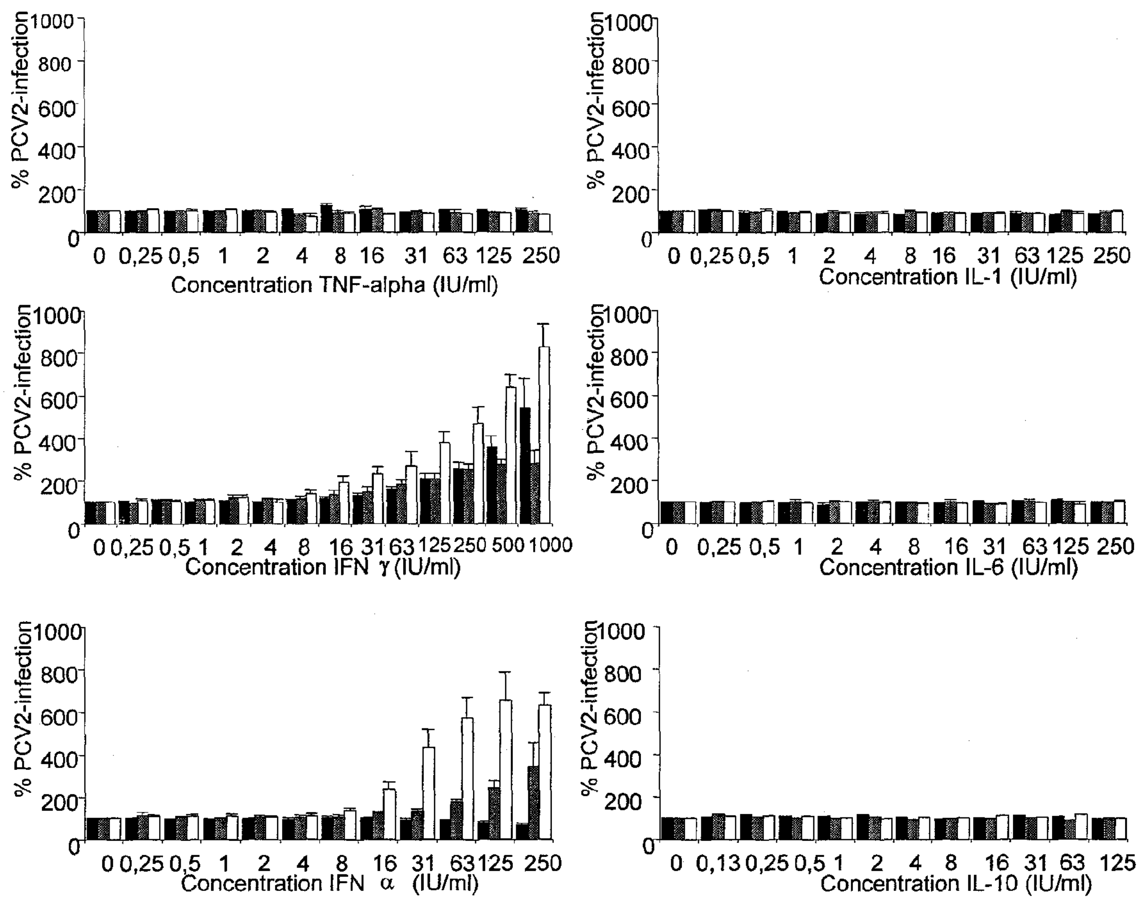
FIG. 1. Influence of cytokines on number of PCV2-infected PK-15 cells according to one embodiment of the invention.

The results of the effects of dilution series of different cytokines in PK-15 cells are shown in FIG. 1. With TNF-alpha, IL-1, IL-6 and IL-10, no significant change in the number of PCV2-positive cells was observed at any concentration or for any time of treatment (before, during or after inoculation). With both interferons (IFN-alpha and IFN-gamma) a clear effect was observed.

IFN-gamma induced a dose-dependent increase in the number of PCV2-antigen positive cells disregarded of the time point when it was added to the medium of the cells (before, during of after the inoculation). The highest effect was seen with the highest concentration tested in the experiment (1000 U/ml). When this concentration of IFN-gamma was supplemented to the medium before inoculation, an increase in positive cell of 518±134% was observed, when it was added to the medium during inoculation, an increase of 270±57% was observed and the highest effect was observed when it was added to the medium after the inoculation, which induced an increase of 791±105%.

The lowest concentration of IFN-gamma which induced a significant increase of PCV2-positive cells when administered before, during or after inoculation, were respectively 16, 2 and 2 U/ml). FIG. 2 shows a picture of light microscopic views of PK-15 cells without IFN (negative controls) and with 500 U/ml IFN-gamma added in the medium after the inoculation.

IFN-alpha induced a similar increase of positive cells when administered during or after inoculation, but it induced a significant reduction of infected cells when the cells were pre-treated. At the highest concentration used (250 U/ml) an increase of 341±114% and 629±59% was observed when added respectively during or after the inoculation. After pretreatment, a reduction of 31±6% was observed. The lowest concentrations of IFN-alpha inducing a significant effect when added before, during or after PCV2-inoculation were respectively 31, 16 and 8 U/ml). The effects induced by treatment of cells with IFN-alpha could be neutralized when IFN-alpha was incubated for 1 hour at 37° C. with IFN-alpha-neutralizing antibodies, prior to incubation with the cells.

Influence of Cytokines on the Total Number of PCV2-Infected 3D4/31 Cells

In 3D4/31 cells, TNF-alpha, IL-1, IL-6 and IL-10, did not induce a significant change in the number of PCV2-positive cells at any concentration or at any time of treatment (before, during of after inoculation). Similar observation were made in these cells compared to PK-15 cells when the 3D4/31 cells were treated with IFN-alpha and IFN-gamma. IFN-gamma induced a dose-dependent increase in the number of PCV2-positive cells when cells were treated before, during or after the inoculation. A maximal increase of respectively 806±88%, 214±16% and 523±115% was observed. When cells were treated with IFN-alpha before inoculation, no significant changes were observed. When IFN-alpha was administered to the cells during or after inoculation, an increase in positive cells of respectively 115±10% and 408±35% was detected. The results of these experiments are presented in FIG. 3.

Example 2

Influence of IFN-Gamma on the Production of PCV2

Since IFN-gamma increased the number of PCV2-positive PK-15 cells independent of the time when it was added to the medium of the cells, this cytokine was selected to investigate the effect in the production of progeny virus at a concentration of 500 U/ml.

The influence of IFN-gamma on the production of progeny virus in PCV2-infected cells was determined by inoculating PK-15 cells with the standard PCV2-stock. After the inoculation, culture medium was added supplemented with IFN-gamma (500 U/ml). At 0, 12, 24, 36, 48 and 72 hours post inoculation (hpi) the supernatant was collected. Subsequently the culture was washed once with 1 ml PBS. Both the supernatant and the washing fluid were centrifuged for 10 minutes at 15,000×g to pellet cells and debris. The centrifuged supernatant and washing fluids were combined and considered to contain the extracellular virus. Both pellets and cell cultures were freeze-thawed tree times and considered to contain the intracellular virus. Intra- and extracellular virus titres were determined by titration on PCV-negative PK-15 cells as described previously.

The results of the production experiment is presented in FIG. 4. Both extracellular and intracellular virus production was increased in the IFN-gamma-treated cells compared to the non-treated control cells. The total PCV2 production in cells treated with IFN-gamma at 72 hpi was 1.3 $\log_{10}$ $TCID_{50}$ higher compared to the non-treated cells.

Example 3

Influence of IFN-Gamma on the Expression Kinetics of PCV2 Proteins

To determine the timing and localisation of PCV2 proteins expression (Capsid protein and REP), PK-15 cells were seeded on glass cover slips and inoculated with PCV2. After inoculation, culture medium was added with or without 500 U/ml IFN-gamma. At 0, 12, 24, 36, 48 and 72 hpi the cells were fixed in methanol at −20° C. Afterwards, a triple immunofluorescence staining was performed to visualize both viral proteins and the cell nucleus. PCV2 capsid protein was detected using purified biotinylated porcine polyclonal anti-PCV2 immunoglobulins which only react with PCV2 capsid proteins. Bound porcine immunoglobulins were visualized with streptavidin conjugated Texas Red (molecular probes, Leiden, The Netherlands). In a second step, the REP protein was detected with a specific mouse monoclonal antibody (F210) visualized with goat-anti-mouse FITC (molecular probes, Leiden, The Netherlands). In a final step, the nuclei of the cells were visualized with Hoechst 33342 (Molecular Probes, Oreg., USA) at a concentration of 0.1 mg/ml. The number of cells with capsid and/or REP protein was counted and the localisation of viral antigens was monitored by fluorescence microscopy.

Treatment of PK-15 cells did not influence the sequence of events considering the expression of PCV2 proteins. Capsid and REP proteins were detected for the first time at respectively 12 and 24 hpi in treated and non-treated cells. The first nuclear localisation of both proteins was observed at 24 hpi in both cultures in a similar proportion of cells.

Example 4

Influence of IFN-Gamma on the Infectious Cycle of PCV2

Since IFN-gamma induced the most constant increase in number of positive cells both in PK-15 cells as in 3D4/31 cells, this cytokine was selected for studies on the influence of interferons on the infectious cycle of PCV2.

a) Influence of IFN-Gamma on the Attachment of PCV2 Capsids on 3D4/31 Cells

The attachment of PCV2 capsids onto untreated 3D4/31 cells and 3D4/31 cells pre-treated with IFN-gamma was studied as described by Misinzo et al. (J Gen Virol. conditionally accepted for publication). Briefly, treated and untreated 3D4/31 cells were chilled on ice and washed before PCV2 capsids were added and allowed to attach for 0, 1, 5, 10, 15, 30 and 60 minutes at 4° C. Unbound PCV2 capsids were washed-off and cells were fixed with 3% (w/v) paraformaldehyde in phosphate-buffered saline with calcium and magnesium (PBS+) at room temperature for 10 minutes. In order to stain the PCV2 capsids, cells were incubated with biotin-conjugated anti-PCV2 swine polyclonal antibodies and streptavidin-FITC (Molecular Probes, Leiden, The Netherlands) for 1 hour at room temperature. The slides were mounted and analysed by acquisition of digital images of stained PCV2 capsids using a Leica TCS SP2 laser scanning spectral confocal system (Leica Microsystems GmbH, Heidelberg, Germany) linked to a Leica DM/IRB inverted microscope (Leica Microsystems GmbH, Wetzlar, Germany). Successive images from the apex to the base of a single cell were taken and merged. The number of PCV2 capsids attached per cell was counted for ten cells at each time point to establish their binding kinetics into 3D4/31 cells.

No differences were observed in the number of attached virion-like particles per 3D4/31 cell, nor on the kinetics of virion binding to the cells as presented in FIG. 5. Both in the treated and non-treated cells, the number of attached virions cells increased quickly within 5 minutes and reached a maximum at 15 minutes after incubation. Attached virions were observed on all cells both treated and non-treated as described before.

b) Influence of IFN-Gamma on the Entry of PCV2

To study the internalization of recombinant capsids on 3D4/31, cells were washed with RPMI-1640 at 37° C. and then incubated with capsids at 37° C. for 15 minutes followed by washing of unbound capsids. Cells were then fixed with a 3% solution of paraformaldehyde (rPBS) for 10 minutes at 30, 60 and 120 minutes since the addition of capsids into the cells, washed with PBS, and permeabilized in a 0.1% Triton X-100 solution in rPBS. Capsids were stained by incubating the calls with a biotin-conjugated anti-PCV2 swine polyclonal antibody followed by streptavidin-FITC (Molecular Probes, Eugene, Oreg.).

A significant increase in the number of internalized virions was observed when 3D4/31 cells were treated with IFN-gamma.

Example 5

Influence of IFN-Gamma on the Number of Infectious Particles Required for the Infection of PK-15 Cells PCV2 infectious titres are generally determined by inoculating 10-fold dilution series on PK-15 cells, followed by a staining of PCV2-positive cells. In this experiment it was investigated if the treatment of PK-15 cells with IFN-gamma before, during or after the inoculation, could increase the sensitivity of the PCV2-titration assay. PK-15 cells were treated with IFN-gamma (500 U/ml) as described above. Subsequently, a PCV2 stock with a known infectious titre was titrated both on treated cells and on non-treated cells. After 72 hours of incubation after inoculation, the cells were fixed and the total number of PCV2-positive cells was determined with the IPMA as described above. The titres obtained in IFN-gamma-treated and non-treated PK-15 cells were compared.

The number of infectious particles needed for infection of PK-15 cells was investigated by titrating a PCV2-stock of a known infectious titre in non-treated (control) and IFN-gamma-treated cells. In non-treated cells the titre of the stock varied between 3.8 and 4.1 $\log_{10}$ $TCID_{50}$/ml. When IFN-gamma was added to the medium after the inoculation of the stock, the titre varied between 5.3 and 5.8 $\log_{10}$, $TCID_{50}$/ml. This indicates that between 1.2 and 2.0 $\log_{10}$ times less infectious PCV2 particles were required for infection of PK-15 cells when they were treated with 500 U/ml IFN-gamma.

Example 6

Effect of Natural Sources of Porcine Cytokines on PCV2-Infection in PK-15 Cells Natural Sources of Porcine Cytokines Two natural sources of interferons were included. First, peripheral blood monocytes (PBMC's) were isolated from blood of a conventional 4-week-old pig by differential centrifugation on Ficoll Paque®. These monocytes were cultured in medium as described earlier (Verfaillie et al. (2002) *Vet Immunol Immunopathol* 81, 97-112) and stimulated with 5 μg/ml concanavalin A (ConA) (Sigma). Simultaneously, a culture of PBMC's was incubated in the same medium without ConA. After 16 hours of incubation at 37° C. in the presence of 5% CO2, the supernatant was collected and centrifuged to remove cells (Verfaillie et al., above). The concentration of IFNγ in these supernatants was respectively 20.5 U/ml and below the detection limit as determined by a porcine IFNγ-specific ELISA (Biosource, Nijvel, Belgium).

Second, 20 times concentrated bronchiolar lavage fluid (BAL-fluid) were collected at 1 day post inoculation from gnotobiotic pigs experimentally inoculated with porcine respiratory coronavirus (PRCV) or mock-inoculated pigs. The BAL-fluid of the PRCV-inoculated pig had previously been determined to contain 174650 U/ml IFNα, 56 U/ml IFNγ, >20480 U/ml IL6 and 273 U/ml TNFα, the BAL-fluid of the mock-inoculated pig contained no detectable levels of IFNα, IFNγ and TNFα and contained 87 U/ml IL6.

Influence of Natural Sources of Porcine Cytokines on the Total Number of PCV2-Infected Cells Two-fold dilutions of the BAL-fluids of the PRCV and mock-inoculated pigs were added to the medium of PCV2-inoculated PK-15 cells after inoculation. Concentrations of the added BAL-fluids ranged from 1.25 to 5%. Supernatants of ConA and mock-stimulated PBMC's were also added to the culture medium of PK-15 cells after inoculation in concentrations ranging from 6.15 to 50%. After 36 hours of incubation, PK-15 cultures were fixed and stained as described above and the number of infected cells was determined.

The results of these experiments are shown in FIG. 6. When 5% of the 20× concentrated BAL fluids of a PRCV-inoculated gnotobiotic pig were added to PK-15 cells after PCV2-inoculation, an increase in PCV2-positive cells of 745±39% was observed. Lower concentrations of this BAL-fluid showed that the effect was dose-dependent. The BAL-fluid of the mock-inoculated gnotobiotic pig did not influence the number of PCV2-positive cells.

The supernatant of ConA-stimulated PBMC's also caused a dose-dependent increase in PCV2-positive cells when it was added to the medium of PCV2-inoculated PK-15 cells. When a concentration of 50% of this supernatant was added to the cells, an increase of 215±22% was observed. Again the supernatant of non-stimulated PBMC's did not influence the number of PCV2-infected cells.

Example 7

Effect of Interferon on the Immune Response to the Vaccination with an Attenuated Circular ssDNA Virus If interferons would increase the replication of PCV2 in vivo, it would probably also increase the replication of attenuated PCV2 and by that mechanism enhance the immune response of the pig to the virus.

Pigs are inoculated with PCV2 (field strain Imp-1121) at 19 days of age. These inoculated pigs are divided in 3 groups. One group contains control pigs (only PCV2). The second group of pigs receives recombinant IFN-gamma (100,000 U per pig every three days). The third group contains pigs that receive ConA (1.5 mg/kg every three days). At different times post inoculation (10, 15, 21 days) samples are collected and the replication of the virus is assessed.

An increase in the replication of PCV2 is detected in pigs injected with IFN-gamma or ConA compared to the control pigs. From this it can be concluded that IFN has a similar effect on PCV2-replication in vivo.

Example 8

Effect of Endosomal-Lysosomal System Acidification Inhibitors on PCV2 Infection of PK-15 Cells Endosomal-lysosomal system acidification was inhibited using lysosomotropic weak bases (ammonium chloride and chloroquine diphosphate) and carboxylic ionophore monensin. All chemical compounds were purchased from Sigma. In a first set of experiments, a two-fold dilution of each inhibitor in PK-15 cells using Stoon-1010 was performed to determine the highest concentration of each inhibitor that exerted the maximal effect without affecting cell viability. Finally, 25 mM ammonium chloride, 125 μM chloroquine diphosphate and 6 μM monensin were chosen. PK-15 cells were cultivated for 24 hours and then inoculated with a dose of PCV2 for 1 hour at 37° C. The viral inoculum was washed-off and cells were further incubated in culture medium with or without inhibitors of endosomal-lysosomal acidification for 24 hours. Then, the culture medium containing endosomal-lysosomal system inhibitors was replaced with fresh culture medium without inhibitors. After the first cycle of PCV2 replication, at 36 hpi, cells were fixed with methanol at −20° C. for 10 minutes. Cells were stored at −20° C. until they were stained using an immunoperoxidase monolayer assay (IPMA) as described by Sanchez et al. (2003, *Vet Microbiol* 95, 15-25).

Results:

The effect of endosomal-lysosomal system acidification inhibitors on PCV2 infection of PK-15 cells is shown in FIG. 7 (white bars). Agents that inhibit endosomal-lysosomal system acidification, ammonium chloride, chloroquine diphosphate and monensin, enhance PCV2 infection compared to control.

Example 9

Synergistic Effect of Endosomal-Lysosomal System Acidification Inhibitors and IFN-Gamma on PCV2 Infection of PK-15 Cells Endosomal-lysosomal system acidification was inhibited using lysosomotropic weak bases (ammonium chloride and chloroquine diphosphate) and carboxylic ionophore monensin as described in Example 8 in the following concentrations: 25 mM ammonium chloride, 125 μM chloroquine diphosphate and/or 6 μM monensin. PK-15 cells were pretreated with or without 500 U/ml IFN-gamma for 24 hours before they were inoculated with the same dose of PCV2 for 1 hour at 37° C. The viral inoculum was washed-off and cells were further incubated in culture medium containing inhibitors of endosomal-lysosomal acidification for 24 hours. Then, the culture medium containing endosomal-lysosomal system inhibitors was replaced with fresh culture medium without inhibitors. After the first cycle of PCV2 replication, at 36 hours post-inoculation cells were fixed with methanol at −20° C. for 10 minutes. Cells were stored at −20° C. until they were stained using an immunoperoxidase monolayer assay (IPMA) as described above. The number of infected cells per well in mock-treated cells inoculated with an equal dose of PCV2 as treated cells was used as the referent, and all results are expressed as a percentage of this referent. All experiments were performed three times, and each condition in a single experiment was performed in duplicate.

Results:

Agents that inhibit endosomal-lysosomal system acidification, ammonium chloride, chloroquine diphosphate and monensin, enhanced PCV2 infection in IFN-gamma treated cells (FIG. 7, black bars). The effect of endosomal-lysosomal system acidification inhibitors was synergistic to that exerted by IFN-gamma, indicating that they increased PCV2 infection via different mechanisms.

Example 10

Synergistic Effect of Endosomal-Lysosomal System Acidification Inhibitors and IFN-Gamma on Progeny PCV2 Production For progeny virus production assays, $2\times10^5$ cells were seeded in every well of 24-well cell culture plates. Cells were pre-treated with or without 500 U/ml IFN-gamma at 6 hours post seeding. At 24 h post-seeding, cells were washed and inoculated with the prototype PCV2 strain Stoon-1010 at an m.o.i. of 0.3 for 1 hour at 37° C. The viral inoculum was washed-off and cells were further incubated in 1 ml of culture medium with or without 25 mM ammonium chloride, 125 μM chloroquine diphosphate and/or 6 μM monensin for 24 hours. Then, the culture medium with or without endosomal-lysosomal system acidification inhibitors was replaced with fresh culture medium without inhibitors. At 1, 24, 48 and 72 hours post-inoculation the supernatant was collected. Subsequently the culture was washed once with 1 ml PBS. Both the supernatant and the washing fluid were centrifuged for 10 minutes at 15,000×g to pellet cells and debris. The centrifuged supernatant and washing fluids were combined and considered to contain the extracellular virus. Both pellets and cell cultures were freeze-thawed three times and considered to contain the intracellular virus. Intra- and extracellular virus titres were determined by titration on PCV-negative PK-15 cells as described previously. Viral antigens were detected using an IPMA as described above and PCV2 titre was expressed as $\log_{10}$ $TCID_{50}$ per $10^5$ cells.

Results:

PCV2 production was increased by treatment of the cells with endosomal-lysosomal system acidification inhibitors and/or IFN-gamma treatment. A synergistic increase in virus production was observed when cells were treated with a combination of endosomal-lysosomal system acidification inhibitors and IFN-gamma (Table 1).

The total PCV2 virus titres in PK-15 cells treated with interferon-gamma and inhibitors of endosomal-lysosomal system acidification is provided in Table 1 and illustrated in FIG. 8.

TABLE 1

Total PCV2 virus titres in PK-15 cells treated with or without 500 U/ml IFN- gamma and/or lysosomotropic agents that inhibit endosomal-lysosomal system acidification.

| Lysosomotropic agent | IFN-gamma (U/ml) | PCV2 titres ($TCID_{50}$ per $10^5$ cells at . . . 1 hpi | 24 hpi | 48 hpi | 72 hpi |
|---|---|---|---|---|---|
| Control | 0 | 1.9 | 1.5 | 2.9 | 3.1 |
| Control | 500 | 2.0 | 2.1 | 3.4 | 3.9 |
| Ammonium chloride | 0 | 2.1 | 1.9 | 3.0 | 3.8 |
| Ammonium chloride | 500 | 1.6 | 3.0 | 4.0 | 4.8 |
| Chloroquine diphosphate | 0 | 1.4 | 1.8 | 3.3 | 4.3 |
| Chloroquine diphosphate | 500 | 1.6 | 2.3 | 4.0 | 4.6 |
| Monensin | 0 | 1.9 | 2.3 | 3.9 | 3.6 |
| Monensin | 500 | 2.0 | 2.8 | 4.6 | 4.8 |

All publications and patents mentioned in this specification are herein incorporated by reference to the same extent as if each individual publication or patent was specifically and individually indicated to be incorporated by reference.

From the foregoing description, one skilled in the art can easily ascertain the essential characteristics of this invention, can make various changes and modifications of the invention to adapt it to various usages and conditions. Thus, other embodiments are also within the claims.

What is claimed is:

1. A medium comprising i) a porcine circovirus, ii) an agent capable of inhibiting endosomal-lysosomal system acidification, and iii) an interferon.

2. The medium of claim 1, wherein said agent is a lysosomotropic agent.

3. The medium of claim 2, wherein said lysosomotropic agent is selected from the group consisting of ammonium chloride, chloroquine diphosphate and monensin.

4. The medium of claim 1, wherein said porcine circovirus is Porcine Circovirus 2 (PCV2).

5. The medium of claim 1, wherein said interferon is interferon alpha or interferon gamma.

6. The medium of claim 1, wherein said interferon is at a concentration of at least 2 U/ml medium.

7. A medium comprising i) a cell-line comprising a porcine circovirus, ii) an agent capable of inhibiting endosomal-lysosomal system acidification, and iii) an interferon.

8. The medium of claim 7, wherein said agent is a lysosomotropic agent.

9. The medium of claim 8, wherein said lysosomotropic agent is selected from the group consisting of ammonium chloride, chloroquine diphosphate and monensin.

10. The medium of claim 7, wherein said interferon is interferon alpha or interferon gamma.

11. The medium of claim 7, wherein said interferon is at a concentration of least 2 U/ml medium.

12. The medium of claim 7, wherein said porcine circovirus is Porcine Circovirus 2 (PCV2).

13. The medium of claim 7, wherein said cell line is a porcine cell line.

14. The medium of claim 13, wherein said porcine cell line is PK-15.

* * * * *